United States Patent [19]

Amimoto et al.

[11] Patent Number: 5,254,754
[45] Date of Patent: Oct. 19, 1993

[54] PROCESS FOR PREPARING ADDUCT OF UNSATURATED ALCOHOL AND IODINATED FLUOROALKANE

[75] Inventors: Yoshio Amimoto; Masaru Hirai; Sueyoshi Ishikawa; Tatsuya Ohtsuka, all of Osaka, Japan

[73] Assignee: Daikin Industries Ltd., Osaka, Japan

[21] Appl. No.: 640,838

[22] Filed: Jul. 14, 1991

[30] Foreign Application Priority Data

Jan. 18, 1990 [JP] Japan .................................. 2-9298

[51] Int. Cl.$^5$ .............................................. C07C 31/34
[52] U.S. Cl. ..................................... 568/842; 568/848
[58] Field of Search ............... 568/841, 842, 850, 848, 568/700

[56] References Cited

U.S. PATENT DOCUMENTS 3,145,222  8/1964  Brace .................................. 568/842
4,073,817  2/1978  Jager .................................. 568/842
4,489,006 12/1984  Krahler .

FOREIGN PATENT DOCUMENTS 0043757  1/1982  European Pat. Off. ............ 568/842

OTHER PUBLICATIONS

Chemical Abstracts, vol. 81, No. 25, Dec. 23, 1974, p. 510.
Park, et al., *J. Org. Chem.*, 26, 2089, 1961.

*Primary Examiner*—Marianne M. Cintins
*Assistant Examiner*—Rebecca Cook
*Attorney, Agent, or Firm*—Birch, Stewart, Kolasch & Birch

[57] ABSTRACT

An adduct of an unsaturated alcohol and an iodinated fluoroalkane is produced at a high conversion and high yield by reacting the unsaturated alcohol and the iodinated fluoroalkane in the presence of a radical catalyst and at least one additive selected from the group consisting of water, basic compounds, metal oxides, silver compounds and epoxy compounds.

8 Claims, No Drawings

PROCESS FOR PREPARING ADDUCT OF UNSATURATED ALCOHOL AND IODINATED FLUOROALKANE

BACKGROUND OF THE INVENTION

1. Field of the Invention

The present invention relates to a process for preparing an adduct of an unsaturated alcohol and an iodinated fluoroalkane.

3-Perfluorooctyl-2-iodo-1-propanol which is one of the adducts is dehydrogeniodinated to give 3-perfluorooctyl-1,2-epoxypropane which is polycondensated with phthalic acid anhydride to form a water- and oil-repellent polymer to be used as a water- and oil-repellent.

2. Description of the Related Art

In general, an adduct of an unsaturated compound and an iodinated fluoroalkane is prepared by reacting the unsaturated compound and the iodinated fluoroalkane in the presence of a radical catalyst.

In such conventional process, if allyl alcohol is used as an unsaturated compound, a conversion of the iodinated fluoroalkane is very low and does not reach 95% at best even when two equivalents of allyl alcohol is addition reacted with one equivalent of the iodinated fluoroalkane. Therefore, after a sufficiently long reaction time, the iodinated fluoroalkane still remains unreacted (see Japanese Patent Kokai Publication No. 69605/1974). Since separation of the unreacted iodinated fluoroalkane from the produced adduct is very difficult, it remains in an intermediate or a final product as an impurity and causes some problems such as liberation of iodine atoms.

SUMMARY OF THE INVENTION

An object of the present invention is to provide a process for preparing an adduct of an unsaturated alcohol and an iodinated fluoroalkane at an improved conversion of the iodinated fluoroalkane.

According to the present invention, there is provided a process for preparing an adduct of an unsaturated alcohol and an iodinated fluoroalkane which comprises reacting the unsaturated alcohol and the iodinated fluoroalkane in the presence of a radical catalyst and at least one additive selected from the group consisting of water, basic compounds, metal oxides, silver compounds and epoxy compounds.

DETAILED DESCRIPTION OF THE INVENTION

As the iodinated fluoroalkane, any iodinated fluoroalkane may be used if it has a $-CF_2I$ group at a molecular end in view of reactivity. The number of carbon atoms is not critical. Preferably, the number of the carbon atoms is from 2 to 500, more preferably, 2 to 100, most preferably 2 to 22. Specific examples of the iodinated fluoroalkane are $CF_3(CF_2)_7I$, $(CF_3)_2CF(CF_2)_6I$, $Cl(CF_2)_8I$, $I(CF_2)_8I$, and the like.

An amount of the unsaturated alcohol is 1.2 to 3 equivalent per one equivalent of the iodinated fluoroalkane. When the amount of the unsaturated alcohol is less than the above lower limit, the conversion is decreased and when it is larger than the above upper limit, the loss is large.

Preferred examples of the unsaturated alcohol are allyl alcohol, methallyl alcohol, crotyl alcohol, 3-methyl-3-butene-1-ol, 1-butene-3-ol, 3-butene 1-ol, etc.

The reaction temperature is preferably from 50° to 120° C., more preferably from 60° to 100° C. When the reaction temperature is lower than 50° C., the reaction rate is too low, and when it is higher than 120° C., amounts of by-products increase so that the yield of the desired product decreases.

The reaction pressure is not critical. In view of a design of a reaction apparatus, atmospheric pressure is preferred.

As the radical catalyst, any one of conventional radical sources can be used. Specific examples of the radical source are azo compounds (e.g. azobisisobutyronitrile (AIBN), azobisdimethylvaleronitrile, azobiscyclohexane carbonitrile, etc.) and peroxides (e.g. benzoyl peroxide, lauroyl peroxide, tert.-butyl hydroxyperoxide, di-tert.-butyl peroxide, etc.).

An amount of water which is used as the additive is from 0.1 to 5 times, preferably from 0.1 to 1 time the weight of the iodinated fluoroalkane. When the amount of water is too small, the conversion is not sufficiently improved, and when it is too large, the reaction rate decreases. When water is added, hydrogen iodide (HI) generated during the reaction is trapped in water and the reaction proceeds without interference.

The same result can be achieved by neutralization with the basic compound. An amount of the basic compound is at least about 0.1% by weight, preferably from 2 to 10% by weight of the iodinated fluoroalkane. Preferably, the basic compound is used in the form of an aqueous solution. In this case, an amount of the aqueous solution of the basic compound can be smaller than the amount of water. The amount of the aqueous solution of the basic compound is at least 1% by weight preferably from 1 to 150% by weight of the iodinated fluoroalkane. Specific example of the basic compound are hydroxides, hydrogencarbonates, carbonates and acetate salts of alkali metals and alkaline earth metals. Preferred examples of the basic compound are NaOH, KOH, $Mg(OH)_2$, $Ca(OH)_2$, $Na_2CO_3$, $K_2CO_3$, $NaHCO_3$, $KHCO_3$, $CH_3COONa$, $CH_3COOK$ and the like.

Amines can be also used as the additive. Examples of the amine are ethylamine, propylamine, isopropylamine, diethylamine, diisopropylamine, triethylamine, diisopropylethylamine, DBU (1,8-diazabicyclo[5.4.0]undec-7-ene), DBN (1,5-diazabicyclo[4.3.0]non-5-ene) and the like.

Further, metal oxides or silver compounds can be used as the additive. Examples of the metal oxide are $Al_2O_3$, $Fe_2O_3$, FeO and ZnO, and examples of the silver compound are $Ag_2O$ and $AgNO_3$. An amount of the metal oxide or the silver compound is at least 0.1% by weight, preferably from 2 to 10% by weight of the iodinated fluoroalkane.

The epoxy compound reacts with HI to form iodohydrin and removes HI in the reaction system, whereby the reaction proceed smoothly. The epoxy compound having a lower boiling point is preferably used since it is easily removed from the produced adduct. However, the epoxy compound having a too low boiling point is difficult to handle.

An amount of the epoxy compound is from 0.01 to 0.3 equivalent per one equivalent of the iodinated fluoroalkane. When the amount of the epoxy compound is to small, the reaction does not proceed smoothly, and when it is too large, the loss is large. Water may be used together with the epoxy compound. Specific examples of the epoxy compound are epichlorohydrin, epibromohydrin, propylene oxide, 1,2-epoxybutane, cyclohexene oxide, 1,2-epoxyhexane, disodium epoxysuccinate, 1,2-epoxydecane, 1,2-epoxydodecane, 1,2-epoxyhexadecane, etc.

PREFERRED EMBODIMENTS OF THE INVENTION

The present invention will be illustrated by following Examples.

EXAMPLE 1

In a 100 ml four-necked flask equipped with a condenser, a thermometer, a stirring bar and a nitrogen gas inlet tube, perfluoro(1-iodooctane) (54.5 g, 0.1 mole), allyl alcohol (8.7 g, 0.15 mole) and water (18.0 g) as an additive were charged and heated on a water bath while stirring and introducing nitrogen gas from the inlet tube. When the mixture temperature reached 70° C., azobisisobutyronitrile (AIBN) (0.5 g) was added and the reaction was carried out while keeping the mixture temperature at 70° C. To find a conversion of perfluoro(1-iodooctane), small amounts of the reaction mixture were sampled at predetermined intervals and analyzed by gas chromatography to confirm a peak assigned to $CF_3(CF_2)_7CH_2CHICH_2OH$ (the reaction product from perfluoro(1-iodooctane) and allyl alcohol) from which peak a content of the product was calculated.

After 4 hours from the addition of AIBN, the peak assigned to perfluoro(1-iodooctane) disappeared. Then, heating and stirring were stopped. The reaction mixture was separated into an upper layer of a yellow liquid and a lower layer of a colorless transparent liquid. The lower layer was recovered by using a separating funnel and washed with hot water (90° C.). A solid material was collected and dried under reduced pressure. A weight of the dried material was 60.0 g. Yield: 98%.

IR (KBr): 3090 (OH) and 1200 $cm^{-1}$.

$^1$H—NMR: $\delta$=2.15 (1H, s, OH), 2.5-3.3 (2H, m, —C$\underline{H}_2$CF$_2$—), 3.87 (2H, d, —C$\underline{H}_2$OH) and 4.4-4.6 (1H, m, —C$\underline{H}$I—).

MS: $\overline{6}$04 (M+), 587, 468,69,31 and 29.

EXAMPLES 2, 3 AND 4

In the same manner as in Example 1 but using an additive shown in Table 1, the reaction was carried out. The results are also shown in Table 1. In Example 4, the conversion after one hour from the addition of AIBN is shown.

COMPARATIVE EXAMPLES 1 AND 2

In the same manner as in Example 1 but using no water and, in Comparative Example 2, adding 0.5 g of AIBN when the reaction mixture temperature reached 70° C., 0.5 g of AIBN after 1.5 hours and 0.5 g of AIBN after 3 hours, the reaction was carried out. The results are shown in Table 1.

EXAMPLES 5 TO 11 AND COMPARATIVE EXAMPLES 3 TO 9

The reaction was carried out under conditions shown in Table 2. In Examples 10 and 11 and Comparative Examples 8 and 9, the amounts of the reactants were reduced to one tenth. The conversion of the iodinated fluoroalkane and the yield of the adduct are shown in Table 2.

The physicochemical data of the products of Examples 6 to 11 are as follows:

EXAMPLE 6

$^1$—H—NMR (CDCl$_3$) $\delta$=2.16 (3H, s, —CH$_3$), 2.34 (1H, t, OH), 2.98 (2H, t, CH$_2$CF$_2$), 3.52 (1H, dd, CH$_2$OH) and 3.77 (1H, dd, CH$_2$OH).

$^{19}$F—NMR (CDCl$_3$): $\delta$=2.3 (3F, t, CF$_3$), 32.6 (2F), 43.2 (6F), 44.1 (2F), 44.8 (2F) and 47.6 (2F). MS: 491 (M+), 471, 441, 73,47 and 29.

EXAMPLES 7 AND 8

$C_8F_{17}$—CH(CH$_3$)—CHI-CH$_2$—OH (2 diastereomers)

First diastereomer

IR (KBr): 3400 and 1200 $cm^{-1}$.

$^1$—H—NMR (CDCl$_3$) $\delta$=1.39 (3H, d, CH$_3$), 1.89 (1H, t, OH), 2.6-3.2 (1H, m, CHCF$_2$), 3.72 (2H, m, CH$_2$O) and 4.71 (1H, ddd, CHI).

$^{19}$F—NMR (CDCl$_3$): $\delta$=1.1 (3F, t, CF$_3$), 33.7 (2F), 40.9 (2F), 42.1 (6F), 43.0 (2F) and 46.4 (2F).

Second diastereomer

IR (KBr): 3400 and 1200 $cm^{-1}$.

$^1$—H—NMR (CDCl$_3$) $\delta$=1.25 (3H, d, CH$_3$), 2.24 (1H, t, OH), 2.4-2.9 (1H, m, CHCF$_2$), 3.4-4.2 (2H, m, CH$_2$O) and 4.47 (1H, ddd, CHI).

$^{19}$F—NMR (CDCl$_3$): $\delta$=2.1 (3F, t, CF$_3$), 36.0 (1F, d, CF$_2$CH$_2$), 38.8 (1F, D, CF$_2$CH$_2$), 42.0 (2F), 43.1 (6F), 44.0 (2F) and 47.4 (2F).

I—CH(CH$_3$)—CH(C$_8$F$_{17}$)—CH2—OH (2 diastereomers)

First diastereomer

IR (KBr): 3420, 2970 and 1200 $cm^{-1}$.

$^1$—H—NMR (CDCl$_3$) $\delta$=1.78 (1H, t, OH), 1.95 (3H, d, CH$_3$), 2.82 (1H, t, CHCF$_3$), 3.96-4.30 (2H, m, CH$_2$O) and 4.75 (1H, dq, CHI).

$^{19}$F—NMR (CDCl$_3$): $\delta$=1.0 (3F, t, CF$_3$), 33.4 (2F, m, CF$_2$CH$_2$), 41.9 (8F), 42.9 (2F) and 46.4 (2F).

Second diastereomer

IR (KBr): 3400 and 1200 $cm^{-1}$.

$^1$—H—NMR (CDCl$_3$): $\delta$=1.81 (1H, t, OH), 2.14 (3H, d, CH$_3$), 2.38 (1H, t, CHCF$_2$), 3.8-4.15 (2H, m, CH$_2$O) and 4.58 (1H, dq, CHI).

$^{19}$F—NMR (CDCl$_3$): $\delta$=1.2 (3F, t, CF$_3$), 34.6 (2F, m, CF$_2$CH$_2$), 42.1 (8F), 43.1 (2F) and 46.5 (2F).

EXAMPLE 9

IR (KBr): 3350 and 1200 $cm^{-1}$.

$^1$—H—NMR (CDCl$_3$): $\delta$=1.95-2.20 (3H, m, CH$_2$CH$_2$OH), 2.20 (3H, s, CH$_3$), 3.00 (2H, t, CH$_2$CF$_2$) and 3.94 (2H, t, CH$_2$O).

$^{19}$F—NMR (CDCl$_3$): $\delta$=2.4 (3F, t, CF$_3$), 32.1 (2, m, CF$_2$CH$_2$), 43.3 (6F), 44.1 (2F), 44.9 (2F) and 47.6 (2F).

MS: 541, 487, 474,467,454,441,71, 55 and 31.

EXAMPLE 10 (2 DIASTEREOMERS)

First diastereomer

M.P. 46°-48° C.

IR (KBr): 3420, 3000 and 1205 $cm^{-1}$.

$^1$—H—NMR (CDCl$_3$): $\delta$=1.31 (3H, d, CH$_3$), 1.68 (1H, brs. OH), 2.6-3.3 (3H, m, CF$_2$C$\underline{H}_2$ & C$\underline{H}$CH$_3$) and 4.38 (1H, dt, CHI).

$^{19}F$—NMR (CDCl$_3$) $\delta = 2.6$ (3F, t, CF$_3$), 34.8 (2F, m, CF$_2$CH$_2$), 43.4 (6F), 44.3 (2F), 45.1 (2F) and 47.8 (2F).
MS: 603, 491, 471, 453, 426, 254, 169, 71, 57 and 43.

Second diastereomer

M.P. 63°-64° C.
IR (KBr): 3360, 3000 and 1210 cm$^{-1}$.

$^1$—H—NMR (CDCl$_3$): $\delta = 1.30$ (3H, d, CH$_3$), 1.92 (1H, brs. OH), 2.82 (2H, dt, CF$_2$CH$_2$), 3.3-3.7 (1H, m, CHCH$_3$), and 4.43 (1H, dt, CHI). p $^{19}F$—NMR (CDCl$_3$): $\delta = 2.2$ (3F, t, CF$_3$), 34.9 (2F, m, CF$_2$CH$_2$), 43.1 (6F), 44.0 (2F), 44.8 (2F) and 47.5 (2F).

MS: 601, 491, 491, 471, 453, 426, 254, 169, 131, 119, 100, 71, 57, 43 and 29.

EXAMPLE 11

M.P. 83°-84° C.
IR (KBr): 3310 and 1200 cm$^{-1}$.

$^1$—H—NMR (CDCl$_3$): $\delta = 1.57$ (1H, brs., OH), 1.9-2.2 (2H, m, CH$_2$CH$_2$O), 2.92 (2H, dt, CH$_2$CF$_2$), 3.6-4.0 (2H, M, CH$_2$O) and 4.52 (1H, m, CHI).

$^{19}F$—NMR (CDCl$_3$) $\delta = 2.0$ (3F, t, CF$_3$), 32.5 (1F, d, CF$_2$CH$_2$), 35.7 (1F, d, CF$_2$CH$_2$), 43.0 (6F), 43.9 (2F), 44.8 (2F) and 47.4 (2F).

MS: 601, 491, 473, 440, 394, 169, 131, 119, 91, 69, 57 and 31.

TABLE 1

| | Example No. | | | | | |
|---|---|---|---|---|---|---|
| | 1 | 2 | 3 | 4 | C.1 | C.2 |
| CF$_3$(CF$_2$)$_7$I (g) | 54.5 | 54.5 | 54.5 | 54.5 | 54.5 | 54.5 |
| Allyl alcohol (g) | 8.7 | 8.7 | 8.7 | 8.7 | 8.7 | 8.7 |
| Additive (g) | H$_2$O (18.0) | H$_2$O (6.0) | Na$_2$CO$_3$ (0.5) H$_2$O (2.0) | Cyclohexene oxide (0.5) | — | — |
| AIBN (g) | 0.5 | 0.5 | 0.5 | 0.5 | 0.5 | 1.5 |
| Temp. (°C.) | 70 | 70 | 70 | 70 | 70 | 70 |
| Conversion (%) | | | | | | |

TABLE 1-continued

| | Example No. | | | | | |
|---|---|---|---|---|---|---|
| | 1 | 2 | 3 | 4 | C.1 | C.2 |
| After 4 hrs. | 100 | 97 | 98 | — | 65 | 92 |
| After 1 hrs. | — | — | — | 100 | — | — |

TABLE 2

CF$_3$(CF$_2$)$_7$I (54.5 g, 0.1 mole) + unsaturated alcohol (0.15 mole) → adduct

| Example No. | Unsaturated alcohol | Additive | Reaction temp. (°C.) | Reaction time (hrs) | Catalyst (g) | Conversion (%) [Yield (%)] |
|---|---|---|---|---|---|---|
| 5 | Allyl alcohol | H$_2$O (18 ml) | 70 | 3.0 | AIBN (0.5) | 95 |
| Com. 3 | ↑ | — | ↑ | ↑ | ↑ | 60 |
| 6 | Methallyl alcohol | H$_2$O (18 ml) | 70 | 5.0 | AIBN (0.5) | 85 [72] |
| Com. 4 | ↑ | — | ↑ | 7.0 | ↑ | 50 [26] |
| 7 | Crotyl alcohol | Cyclohexene oxide (0.03 mole) | 110 | 2.5 | (t-BuO—)$_2$ (0.44) | 98 [74] |
| Com. 5 | ↑ | — | ↑ | 5.0 | ↑ | 60 [22] |
| 8 | ↑ | H$_2$O (18 ml) | 70 | 5.0 | AIBN (0.5) | 62 [50] |
| Com. 6 | ↑ | — | ↑ | 3.0 | ↑ | 42 [21] |
| 9 | 3-Methyl-3-butene-1-ol | H$_2$O (18 ml) | 70 | 2.0 | AIBN (0.5) | 95 [69] |
| Com. 7 | ↑ | — | ↑ | ↑ | ↑ | 63 [18] |
| 10 | 1-Butene-3-ol | H$_2$O (2 ml) | 70 | 5.0 | AIBN (0.05) | 87 [76] |
| Com. 8 | ↑ | — | ↑ | 5.5 | ↑ | 20 [15] |
| 11 | 3-butene-1-ol | H$_2$O (4 ml) | 70 | 2.0 | AIBN (0.05) | 100 [95] |
| Com. 9 | ↑ | — | ↑ | 5.0 | ↑ | 71 [65] |

What is claimed is:

1. A process for preparing an addition product of an alkenol and a 1-iodofluoroalkane which comprises reacting the alkenol and the 1-iodofluoroalkane in the presence of at least one catalyst selected from the group consisting of azo compounds and peroxides and at least one additive selected from the group consisting of water, a salt of an alkali metal or an alkaline earth metal with a weak acid, silver nitrate and an alkyl oxirane or halooxirane.

2. The process according to claim 1, wherein said 1-iodofluoroalkane has a —CF$_2$I at a molecular end.

3. The process according to claim 1, wherein 1.2 to 3 equivalent of said alkenol is reacted with one equivalent of said 1-iodofluoroalkane.

4. The process according to claim 1, wherein said additive is water and added in an amount of 0.1 to 1.0 times the weight of said 1-iodofluoroalkane.

5. The process according to claim 1, wherein said additive is a salt of an alkali metal or an alkaline earth metal with a weak acid and added in an amount of at least 2% by weight of said 1-iodofluoroalkane.

6. The process according to claim 1, wherein said additive is a silver nitrate and added in an amount of at least 2% by weight of said 1-iodofluoroalkane.

7. The process according to claim 1, wherein said additive is an alkyl oxirane or halooxirane and added in an amount of 0.01 to 0.3 equivalent per one equivalent of said 1-iodofluoroalkane.

8. The process according to claim 1, wherein the alkyl oxirane or halooxirane is selected from the group consisting of epichlorohydrin, epibromohydrin, propylene oxide, 1,2-epoxybutane, cyclohexene oxide, 1,2-epoxyhexane, disodium epoxysuccinate, 1,2-epoxydecane, 1,2-epoxydodecane, 1,2-epoxyhexadecane.

* * * * *

UNITED STATES PATENT AND TRADEMARK OFFICE
CERTIFICATE OF CORRECTION

PATENT NO. : 5,254,754
DATED : Oct. 19, 1993
INVENTOR(S) : Amimoto et al.

It is certified that error appears in the above-indentified patent and that said Letters Patent is hereby corrected as shown below:

Title page, item: "[22] Filed:" change "Jul. 14, 1991" to --Jan. 14, 1991--.

Signed and Sealed this

Fifth Day of April, 1994

Attest:

BRUCE LEHMAN

*Attesting Officer*    *Commissioner of Patents and Trademarks*